US005968932A

United States Patent [19]

Winokur et al.

[11] Patent Number: 5,968,932

[45] Date of Patent: Oct. 19, 1999

[54] METHOD OF INHIBITING SLEEP APNEA

[75] Inventors: Andrew Winokur, Merion; Allan I. Pack, Glen Mills, both of Pa.

[73] Assignee: Gruenenthal GmbH, Aachen, Germany

[21] Appl. No.: 09/051,859

[22] PCT Filed: Oct. 24, 1996

[86] PCT No.: PCT/US96/17184

§ 371 Date: Oct. 28, 1998

§ 102(e) Date: Oct. 28, 1998

[87] PCT Pub. No.: WO97/15309

PCT Pub. Date: May 1, 1997

Related U.S. Application Data

[60] Provisional application No. 60/006,032, Oct. 24, 1995.

[51] Int. Cl.[6] .......... A61K 31/54

[52] U.S. Cl. .......... 514/227.8

[58] Field of Search .......... 514/227.8

[56] References Cited

PUBLICATIONS

Heal et al., Neuropharmacology 20/10 (947–957) (abstract), 1981.

Bayliss et al., “Thyrotropin–Releasing Hormone Causes Excitation of Rat Hypoglossal Motoneurons In Vitro”, *Sleep* 16:S49–S52 (1993).

Pack et al., “Obstructive Sleep Apnea”, *Advances in Internal Medicine* 39:517–567 (1994).

“Catching Some . . . ZZZZZZZZs”, *The Herald Journal,* Jul. 11, 1995, p. 13.

*Primary Examiner*—Phyllis Spivack
*Attorney, Agent, or Firm*—Evenson, McKeown, Edwards & Lenahan, P.L.L.C.

[57] ABSTRACT

A method of inhibiting sleep apnea is disclosed comprising administering an effective amount of 6-methyl-5-oxo-3-thiomorpholinylcarbonyl-L-histidine-L-prolinamide or a pharmaceutically acceptable acid addition salt thereof.

13 Claims, No Drawings

METHOD OF INHIBITING SLEEP APNEA

This case is a 371 of PCT/U.S. Pat. No. 96/17,184 filed Oct. 24, 1996.

BACKGROUND OF THE INVENTION

Obstructive sleep apnea is a serious disorder in which normal breathing during sleep is interrupted for periods of 10 seconds to a minute or even longer as a result of obstruction of the upper airway. Sleep apnea syndrome also involves decreases in blood oxygen levels. To resume breathing and restore blood oxygen, the subject must wake up. Thus, normal sleep is interrupted. Sleep apnea may be classified as mild, five to 25 events per hour; moderate, 25 to 40 events per hour; or severe more than 40 events per hour. Persons with sleep apnea are prevented from attaining essential rest and suffer from chronic sleep fragmentation/deprivation occurring as a consequence of frequent nightly arousals brought about by critical decreases in blood oxygen levels secondary to disruptions in respiration. It has been estimated that from 1 to 3 percent of the adult population of North America suffers from sleep apnea. Sleep apnea has been associated with increased risk of heart attacks or strokes. Sleep apnea sufferers also frequently experience excessive daytime sleepiness which can result in them suddenly falling asleep while engaged in activities requiring alertness, such as driving a car.

Although consideration has been given to the possibility of treating sleep apnea with drugs such as medroxyprogesterone, protriptyline, acetazolamide, nicotine or even strychnine, there is currently no satisfactory pharmacotherapy for sleep apnea. Instead, sleep apnea is commonly treated either by throat surgery designed to maintain airway patency during sleep or with mechanical devices such as dental retainers. Surgery to remove tissues thought to contribute to obstruction of the airway is effective in only about 50 to 60% of patients. Cases of obstructive sleep apnea are generally managed with apparatus known as a continuous positive airway pressure (CPAP) machine. The CPAP comprises a mask that fits over the nose of the patient. The mask has an hose attached to it and a small box with a fan that blows air through the hose and into the nasal passages. The CPAP machine provides positive air pressure in the patient airway in order to prevent collapse of the airway which initiates a sleep apnea episode. While the CPAP is generally effective if used consistently, it is also expensive, cumbersome and highly inconvenient, thereby giving rise to significant patient compliance problems.

Thus, there has remained a substantial need for improved methods of treating obstructive sleep apnea, and particularly for an effective pharmacotherapy for treating this disorder.

SUMMARY OF THE INVENTION

Accordingly, it is the object of the present invention to provide a method of treating patients suffering from obstructive sleep apnea.

A further object of the invention is to provide an effective pharmacotherapeutical treatment method for obstructive sleep apnea.

Yet another object of the invention is to provide an effective treatment method for obstructive sleep apnea which avoids the use of surgery or cumbersome mechanical devices.

These and other objects are achieved in accordance with the present invention by providing a method of inhibiting sleep apnea in a mammal comprising administering to said mammal an effective sleep apnea inhibiting amount of 6-methyl-5-oxo-3-thiomorpholinylcarbonyl-L-histidyl-L-prolinamide.

DETAILED DESCRIPTION OF THE PREFERRED EMBODIMENTS

The preferred active form of 6-methyl-5-oxo-3-thiomorpholinylcarbonyl-L-histidyl-L-prolinamide is (3R, 6R) -N- [(6-methyl-5-oxo-3-thiomorpholinyl) carbonyl]-L-histidyl-L-prolinamide tetrahydrate. For convenience, this substance will be referred to hereinafter by its international, non-proprietary name, Montirelin. Montirelin is a known compound which exhibits central nervous system stimulating effects. It has been suggested for possible use as an anti-depressant or in the treatment of loss of consciousness caused by head concussion. The preparation of this compound is described e.g. in Schwertner et al., U.S. Pat. No. 4,045,556, the disclosure of which is incorporated herein by reference.

Montirelin may be administered in various ways. For reasons of patient convenience, orally administrable forms are desirable. It may also be successfully administered by intravenous injection of sterile solutions. Preferred dosages may range from about 0.05 mg/kg/day to about 50 mg/kg/day. Dosages in the range from about 200 $\mu$g/kg/day to about 400 $\mu$g/kg/day are particularly preferred. It is understood that the optimum dosage may vary depending on the patient and the severity of the condition being treated, and it is considered within the skill of the art to optimize the dosage within the indicated range.

The active substance may be administered as such as a free base or in the form of a salt with a pharmaceutically acceptable inorganic acid, such as hydrochloric acid, sulfuric acid or phosphoric acid, or organic acid such as acetic acid, benzoic acid, maleic acid, fumaric acid, tartaric acid, benzene sulfonic acid, etc.

The active substance may be formulated in the form of sterile solutions or in tablets, capsules, dragees, syrups, granules, suppositories, sprays, etc. with various known pharmaceutical carriers or diluents such as water, mineral oil, syrups, polyethylene glycol, lactose, corn starch, paraffin and the like, and may be mixed with known adjuvants such as stabilizers, suspending agents, binders, viscosity improvers, flavors, coloring agents, preservatives, etc.

For purposes of illustration, useful dosage forms may be prepared as follows:

Example Oral Tablet Formulation

Tablets may be prepared comprising the following ingredients in parts by weight:

| Ingredient | Parts |
|---|---|
| Montirelin | 10 parts |
| lactose monohydrate | 64 parts |
| corn starch | 20 parts |
| polyvinylpyrrolidone (Polyvidone K 30) | 5 parts |
| magnesium stearate | 1 part |

The active compound, lactose monohydrate and corn starch are sieved through a 0.63 mm sieve, mixed in a cube blender for 10 minutes, granulated with an aqueous solution of polyvinylpyrrolidone in water (50 g in 200 ml of water), dried, sized through an 0.8 mm sieve together with the magnesium stearate, mixed and pressed into tablets having a diameter of 6 mm and an average weight of 100 mg using a conventional tablet press such as a Korsch EK 0 eccentric press.

Example Oral Liquid Formulation

An orally administrable liquid formulation may be prepared comprising the following ingredients in parts by weight:

| | |
|---|---|
| Montirelin | 10 parts |
| potassium sorbate | 10 parts |
| sodium citrate | 6 parts |
| citric acid | 2 parts |
| sodium chloride | 2 parts |
| sucrose | 200 parts |

sufficient water to make desired solution volume containing 10 g Montirelin per liter of solution. The solid ingredients were all dissolved in water, filtered through a 0.23 μm membrane and filled into bottles. 1 ml of the resulting solution contained 10 mg of Montirelin. Individual dosing can be achieved by administering individual volumes of the solution to the patient.

Example Nasal Spray Formulation

A nasal spray formulation may be prepared comprising the following ingredients in parts by weight:

| | |
|---|---|
| Montirelin | 80 parts |
| benzalkonium chloride | 1 part |
| polyoxyethylene (20) sorbitan monooleate (Polysorbate 80) | 80 parts |
| sodium carboxymethylcellulose (Tylose ™ C 30) | 80 parts |
| disodium hydrogen phosphate | 72 parts |
| sodium dihydrogen phosphate | 32 parts |
| dextrose | 240 parts |

purified water to make desired solution volume containing 10 g Montirelin per liter of solution.

The solid ingredients were all dissolved in the water, filtered through a 0.5 μm membrane and, filled into bottles topped by a spray pump with a volumetric dispensing chamber of 100 μl for nasal administration.

Toxicity

The subacute repeated-dose intravenous toxicity of Montirelin was investigated in Sprague-Dawley rats treated repeatedly at 0.05, 0.5,5 and 50 mg/kg/day for five weeks, and the reversibility of its toxic effects was also investigated by a four-week recovery study.

Eight nine SPF Slc:SD rats of both sexes (age: four weeks, body weight: 70.0–81.6 g) were purchased from Shizuoka Agriculture Cooperative Association for Laboratory Animals. During a one-week quarantine/acclimation period, the animals were measured for body weight and observed for any general symptoms, and healthy animals showing normal growth were selected and used in the experiment at the age of five weeks.

Males and females were used in five groups (including the control group) of 10 animals/sex, and additional 10 animals/sex were added to the control, 0.5 mg/kg and 50 mg/kg groups to investigate the reversibility of the toxic effect of the test substance. All these animals were randomized to each group by weight stratification so that the differences in initial mean body weight were within 2% between groups. At the start of the treatment, the body weight was 116.5–132.9 g for males and 107.0–123.4 g for females.

The maximal dose was set at 50 mg.kg which is three lower doses were set at 5, 0.5 and 0.05 mg/kg using a common ratio of 1/10. This study also included the vehicle control group.

The experimental design (doses, number of animals/group and concentrations of the dosing solution) is presented in Table I.

TABLE I

Subacute toxicity study of Montirelin in rats

| | | Number of animals | | Volume of Test Substance | |
|---|---|---|---|---|---|
| | | Administration period (5 weeks) | | | |
| Sex | Group | Recovery period (4 weeks) | | (ml/Kg) | (W/V %) |
| Male | Control* | 20 | 10 | 5 | 0 |
| | 0.0 mg/kg | 10 | — | 5 | 0.001 |
| | 0.5 mg/kg | 20 | 10 | 5 | 0.01 |
| | 5 mg/kg | 10 | — | 5 | 0.1 |
| | 50 mg/kg | 20 | 10 | 5 | 1 |
| Female | Control* | 20 | 10 | 5 | 0 |
| | 0.0 mg/kg | 10 | — | 5 | 0.001 |
| | 0.5 mg/kg | 20 | 10 | 5 | 0.01 |
| | 5 mg/kg | 10 | — | 5 | 0.1 |
| | 50 mg/kg | 20 | 10 | 5 | 1 |

*physiological saline

Dosing solutions were prepared by dissolving a weighed amount of the test substance in physiological saline at a concentration of 1 W/V % using a volumetric flask. Lower dosing solutions were obtained by successive 10-fold dilution of the initial solution. The respective dosing solution was repeatedly administered intravenously once daily for 35 days into the tail vein at a rate of 0.2 ml/10 sec. using a 1/4 syringe for injection. The treatment was given at a constant volume of 0.5 ml/100 g body weight in all dose groups, and the control group was treated with physiological saline at the same volume in the same manner.

Clinical signs in all animals were observed daily between two and four hours after dosing according to Irwin's method of comprehensive observational assessment, and the type, severity, onset time and disappearance time of toxic symptoms were recorded. During the recovery period, the clinical observation was performed once daily in the morning in the same manner. The body weight, food consumption and water consumption were measured in all animals three times weekly in the morning throughout the treatment and recovery periods and recorded.

Throughout the administration and recovery periods, no death occurred in any treatment or control groups.

1. In the 50 mg/kg group, systemic tremor was observed transiently during the injection in both sexes form day 0 (the initial dosing day), but this symptom gradually regressed from day 1 with increasing day of treatment, disappearing by day 6 in males and by day 4 in females. In the 5 mg/kg or higher groups, almost all males and females showed transient polyuria, and this effect peaked at about one hour after dosing from day 0–3. However, this symptom also regressed as the treatment day increased, disappearing by day 4–28. There were no other remarkable clinical signs throughout the administration and recovery periods.

2. The water consumption increased in both sexes receiving 5 mg/kg or above from day 2–3 until about week 4. Treated males tended to decrease food consumption as compared with the control males, and, reflecting this effect, the body weight gain was suppressed in males, particularly those receiving 0.5, 5 and 50 mg/kg. In females, changes in food consumption and body weight were unremarkable.

3. The urinary findings were unremarkable except for an increase in urine volume in males receiving 5 mg/kg or above and females receiving 5 mg/kg or above at week 2 and 5 of treatment.

4. Hematologically, both sexes receiving 50 mg/kg showed increasing tendency in red blood cell count, hemoglobin and hematocrit to increase and decreasing tendency in total white blood cell count. However, all these changes were within the range of normal physiological variations. Changes in other hematological parameters were not related to the dose.

5. No treatment-related abnormalities were observed in the blood biochemical parameters.

6. At autopsy, no treatment-related grossly abnormal changes ere observed. Histopathologically, the incidence of hypertrophy of serous cells in the submaxillary gland showed dose-dependency in both sexes of all treatment groups. In other organs, no remarkable changes were shown at the light microscopic level, nor were there any abnormal changes in the liver or kidney at the electron microscopical examination.

All observed changes were reversed by discontinuing administration of the active compound.

EXAMPLE 1

The efficacy of Montirelin in treating obstructive sleep apnea was demonstrated in a standard English bulldog test model. Five bulldogs were implanted with subcutaneous electroencephalogram (EEG) electrodes and instrumented with respiratory oscillation belts (Respitrace™) to measure abdominal and ribcage movements and with an ear oximeter to measure oxygen saturation ($SaO_2$). Each dog was observed for an eight hour period, and waking and sleep behavior was noted. Montirelin in a sterile saline vehicle was administered intravenously to the test animals at a dosage of 100 μg/kg. Each test with active substance was preceded by a control day in which only the saline vehicle was administered. The effect of Montirelin on hypersomnolence and sleep disordered breathing was assessed.

Hypersomnolence was determined by sleep latency and total sleep time. Total sleep time (TST) is expressed as a percentage calculated by dividing the total sleep time in minutes by the total study time in minutes and multiplying the resulting quotient by 100 according to the formula:

$$\% \, TST = \frac{\text{Total Sleep Time (min.)}}{\text{Total Study Time (min.)}} \times 100$$

The results are shown in the following Table II:

TABLE II

| Test Dog No. | TST (%) Saline Control | TST (%) Montirelin |
|---|---|---|
| 1 | 16.0 | 18.5 |
| 2 | 16.7 | 17.0 |
| 3 | 26.4 | 26.7 |
| 4 | 32.6 | 17.0 |
| 5 | 12.6 | 3.0 |
| Average | 20.9 ± 8.3 | 16.4 ± 8.5 |

Sleep latency was defined as the total minutes until the onset of non-REM sleep. The results observed during the test are shown in the following Table III:

TABLE III

| Test Dog No. | Sleep Latency (min) Saline Control | Sleep Latency (min) Montirelin |
|---|---|---|
| 1 | 113 | 47 |
| 2 | 79 | 149 |
| 3 | 79 | 145 |
| 4 | 93 | 150 |
| 5 | 93 | 219 |
| Average | 91.4 ± 14 | 142 ± 61.4 |

Sleep disordered breathing was evaluated in terms of a sleep disordered breathing index (SDBI) defined as the total number of rapid eye movement (REM) events divided by a quantity equal to the total REM time divided by 60 minutes according to the formula:

$$SDBI = \frac{REM \text{ Event Total}}{\frac{\text{Total } REM \text{ Time}}{\text{60 minutes}}}$$

A REM event (apnea) is defined as an incident of decreased or absent respiration and a decrease of 4% or more in the saturated blood oxygen ($SaO_2$) level occurring during REM sleep. The results of the sleep disordered breathing test are tabulated in the following Table IV:

TABLE IV

| Test Dog No. | SDBI Saline Control | SDBI Montirelin |
|---|---|---|
| 1 | 4.4 | 7.2 |
| 2 | 17.5 | 8.2 |
| 3 | 15.5 | 2.6 |
| 4 | 8.7 | 0.0 |
| 5 | 33.2 | 25.7 |
| Average | 15.9 ± 11 | 8.7 ± 10 |

It can be seen that Montirelin produced an approximately 50% reduction in sleep disordered breathing associated with only a slight reduction in total sleep time. Although sleep may be somewhat shallower, the Montirelin-treated test animals awaken less frequently and thus exhibit markedly better consolidated sleep patterns.

EXAMPLE 2

In a further experiment, Montirelin was administered on different days at varying dosage levels to one bulldog with moderately severe obstructive sleep apnea. In this bulldog, a double-blind study was conducted in which saline was administered as a control and four different doses of Montirelin (100 mg/kg, 200 mg/kg, 400 mg/kg and 800 mg/kg) were administered. The dog was studied on four different days at each dose of the active compound. On each day the dog was observed for six hours following administration of the drug or control by i.v. injection. The order of different doses of drug or saline control was randomized, and a wash-out period of two days was allowed after study of a particular dose. During the studies, respiratory movement, oxygen saturation and electroencephalogram for sleep state were measured. The number of sleep-disordered breathing events or respiratory disturbance incidents (RDI) per hour was calculated according to the formula given above both for non-rapid eye movement (non-REM) sleep, which occupies the majority of sleep time, and rapid eye movement (REM) sleep. Mean sleep efficiency and arousal index were also determined. The results are shown in the following Table V:

TABLE V

| Montirelin Level | Saline Control | 100 mg/kg | 200 mg/kg | 400 mg/kg | 800 mg/kg |
|---|---|---|---|---|---|
| Mean Sleep Efficiency | 39% | 41% | 37% | 40% | 38% |
| Arousal Index | 12 | 16 | 7 | 12 | 6* |
| non-REM Sleep RDI | 6 | 8 | 0* | 4 | 2* |
| REM Sleep RDI | 44 | 53 | 70 | N/A | N/A |
| Lowest $O_2$ Saturation | 89 | 92 | 86 | 92 | 93 |

*$p < 0.05$

The data show that there is a significant reduction in non-REM sleep-disordered breathing events at drug levels of 200 mg/kg and above. In this test animal, there does not appear to have been an impact on REM sleep RDI at lower dose levels. At higher dosages of 400 mg/kg and 800 mg/kg, the animal did not enter REM sleep, so that the number of REM sleep breathing episodes could not be studied at these dose levels. The active compound did not affect sleep efficiency, but did reduce the number of arousals per hour. There was no effect on oxyhemoglobin saturation during breathing episodes. These results show that Montirelin produces a dose-dependent reduction in the number of episodes where breathing declines during non-REM sleep, and thereby indicate that Montirelin administration may be considered to show promise as a treatment for alleviating non-REM sleep disordered breathing.

In practice, Montirelin may be administered as a bolus from 0 to 12 hours, preferably from 0.2 to 6 hours, prior to a normal sleeping period. The active compound may be administered orally or parenterally, e.g. by intramuscular injection, subcutaneous injection, intranasal inhalation, rectal administration or intravenous administration.

Without being bound to any theory, it is believed that Montirelin acts by potentiating the activity of motoneurons controlling the musculature of the airway during sleep, thereby preventing the loss of muscle tone associated with obstructive events.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of inhibiting sleep apnea in a mammal comprising administering to said mammal an effective sleep apnea inhibiting amount of 6-methyl-5-oxo-3-thiomorpholinylcarbonyl-L-histidyl-L-prolinamide or a pharmaceutically acceptable salt thereof.

2. A method according to claim 1, wherein 6-methyl-5-oxo-3-thiomorpholinylcarbonyl-L-histidyl-L-prolinamide is administered by intravenous injection of a sterile isotonic saline solution thereof.

3. A method according to claim 1, wherein 6-methyl-5-oxo-3-thiomorpholinylcarbonyl-L-histidyl-L-prolinamide is administered at a dosage of from about 0.05 mg/kg/day to about 50 mg/kg/day.

4. A method according to claim 3, wherein 6-methyl-5-oxo-3-thiomorpholinylcarbonyl-L-histidyl-L-prolinamide is administered at a dosage in the range from about 200 μg/kg/day to about 400 μg/kg/day.

5. A method according to claim 3, wherein 6-methyl-5-oxo-3-thiomorpholinylcarbonyl-L-histidyl-L-prolinamide is administered at a dosage of about 100 μg/kg/day.

6. A method according to claim 1, wherein 6-methyl-5-oxo-3-thiomorpholinylcarbonyl-L-histidyl-L-prolinamide or a pharmaceutically acceptable salt thereof is administered as a bolus from 0 to 12 hours prior to a normal sleeping period.

7. A method according to claim 1, wherein 6-methyl-5-oxo-3-thiomorpholinylcarbonyl-L-histidyl-L-prolinamide or a pharmaceutically acceptable salt thereof is administered orally.

8. A method according to claim 1, wherein 6-methyl-5-oxo-3-thiomorpholinylcarbonyl-L-histidyl-L-prolinamide or a pharmaceutically acceptable salt thereof is administered parenterally.

9. A method according to claim 8, wherein 6-methyl-5-oxo-3-thiomorpholinylcarbonyl-L-histidyl-L-prolinamide or a pharmaceutically acceptable salt thereof is administered by intramuscular injection.

10. A method according to claim 8, wherein 6-methyl-5-oxo-3-thiomorpholinylcarbonyl-L-histidyl-L-prolinamide or a pharmaceutically acceptable salt thereof is administered by intranasal inhalation.

11. A method according to claim 8, wherein 6-methyl-5-oxo-3-thiomorpholinylcarbonyl-L-histidyl-L-prolinamide or a pharmaceutically acceptable salt thereof is administered intravenously.

12. A method according to claim 8, wherein 6-methyl-5-oxo-3-thiomorpholinylcarbonyl-L-histidyl-L-prolinamide or a pharmaceutically acceptable salt thereof is administered subcutaneously.

13. A method according to claim 8, wherein 6-methyl-5-oxo-3-thiomorpholinylcarbonyl-L-histidyl-L-prolinamide or a pharmaceutically acceptable salt thereof is administered rectally.

* * * * *